US00PP18806P3

(12) United States Plant Patent
Ackerman

(10) Patent No.: US PP18,806 P3
(45) Date of Patent: May 13, 2008

(54) RASPBERRY PLANT NAMED 'PS-1852'

(50) Latin Name: *Rubus idaeus*
Varietal Denomination: PS-1852

(75) Inventor: Stephen M. Ackerman, Salinas, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 11/640,239

(22) Filed: Dec. 18, 2006

(65) Prior Publication Data

US 2007/0150990 P1 Jun. 28, 2007

Related U.S. Application Data

(60) Provisional application No. 60/752,948, filed on Dec. 23, 2005.

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
*Assistant Examiner*—S. B. McCormick-Ewoldt
(74) *Attorney, Agent, or Firm*—Foley & Lardner LLP

(57) ABSTRACT

This invention relates to a new and distinct variety of raspberry plant named 'PS-1852'. The new variety is primarily adapted to the growing conditions of the central coast of California and is characterized by the following: large upright primocanes, late fall primocane production, early spring floricane production, large conical berries, with nearly ⅔ of the total production coming from the floricane. Foliage is strongly concave, medium green; possessing very strong rugosity, and always 3-foliage. Primocanes have a weak waxy coat, dense thorns, and weak to medium anthocyanin coloration.

4 Drawing Sheets

Latin name of the genus and species of the plant claimed: *Rubus idaeus*.
Variety denomination: 'PS-1852'.

BACKGROUND OF THE INVENTION

The present invention relates to a new and distinct raspberry variety designated as 'PS-1852'. This new variety is a result of a controlled cross made by the inventor, Stephen M. Ackerman, in 1995 between raspberry variety 'PS-1094' (an unpatented Plant Sciences, Inc. selection) and raspberry variety 'PS-1316' (an unpatented selection). The variety is botanically known as *Rubus idaeus*.

The seedling resulting from the aforementioned cross was asexually propagated by dormant canes in Santa Cruz County, Calif. and was subsequently selected by the inventor from a controlled breeding plot in Watsonville, Calif. in 1997. After its selection, the new variety was further asexually propagated by dormant canes, roots and non-dormant root shoot cuttings in both Santa Cruz County, Calif. and San Joaquin County, Calif. The new variety was then extensively tested over the next several years in fruiting fields in Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'PS-1852' is primarily adapted to the climate and growing conditions of the central coast of California. This region provides the necessary year-round temperatures required for it to produce and maintain a strong vigorous plant and to remain in fruit production from August through December on primocanes and in the ensuing year from May through July on the floricanes. The following traits have been repeatedly observed and are determined to be unique characteristics of 'PS-1852', which in combination distinguish this raspberry plant as a new and distinct variety:

1. Large plant size;
2. Late fall primocane production;
3. Early spring floricane production; and
4. Large fruit size.

The raspberry varieties that are believed to be most closely related to the new raspberry variety 'PS-1852' are the raspberry variety 'PS-1049' (patented, U.S. Plant Pat. No. PP 10,142), and the raspberry variety 'PS-1703' (patented, U.S. Plant Pat. No. PP 15,151).

In comparison to the similar raspberry varieties 'PS-1049' and 'PS-1703', 'PS-1852' differs by the following combination of characteristics described in Table 1:

TABLE 1

| Characteristic | 'PS-1852' | 'PS-1049' (U.S. PP 10,142) | 'PS-1703' (U.S. PP 15,151) |
|---|---|---|---|
| 1. Primocane length (m) | 2.2 | 2.0 | 1.8 |
| 2. Basal diameter (mm) | 18.6 | 16.4 | 15.3 |
| 3. Internode length of central ⅓ (cm) | 3.8 | 5.0 | 5.8 |
| 4. Predominate number of leaflets | Always 3 | Equal 3-5 | Mostly 5 |
| 5. Leaf color (upper side) | 7.5GY 3/4 to 3/6 | 7.5GY 3/4 to 4/4 | 7.5GY 2/4 to 3/4 |

TABLE 1-continued

| Characteristic | 'PS-1852' | 'PS-1049' (U.S. PP 10,142) | 'PS-1703' (U.S. PP 15,151) |
|---|---|---|---|
| 6. Leaf shape (cross section) | Strongly concave | Slightly concave | Slightly concave to slightly convex |
| 7. Rugosity | Very strong | Medium | Medium to strong |
| 8. Percent of primocane fruiting | 27% | 40% | 46% |
| 9. Primocane color | 10Y 7/4 to 7/6 | 5GY 7/4 to 6/4 | 7.5GY 6/2 to 6/4 |
| 10. Floricane color | 2.5YR 3/4 to 7.5YR 4/6 | 5YR 4/4 to 4/6 | 5YR 4/4 to 4/6 |
| 11. Bloom intensity | Weak | Strong | Medium to strong |
| 12. Thorn density per cm of central ⅓ | 7.2 | 4.0 | 4.5 |

For identification a series of molecular markers have been determined for this new variety.

BRIEF DESCRIPTION OF THE DRAWINGS

The accompanying color photographs illustrate the overall appearance of typical specimens of the new raspberry variety, 'PS-1852', at various stages of development as true as reasonably possible with color reproductions of this type. Color in the photographs may differ slightly from the color value cited in the detailed botanical description which accurately describes the color of 'PS-1852'. The depicted plant and plant parts of the new raspberry variety 'PS-1852' were taken in Watsonville, Calif. and are approximately 7 to 10 months old.

DETAILED BOTANICAL DESCRIPTION

Figure 1:
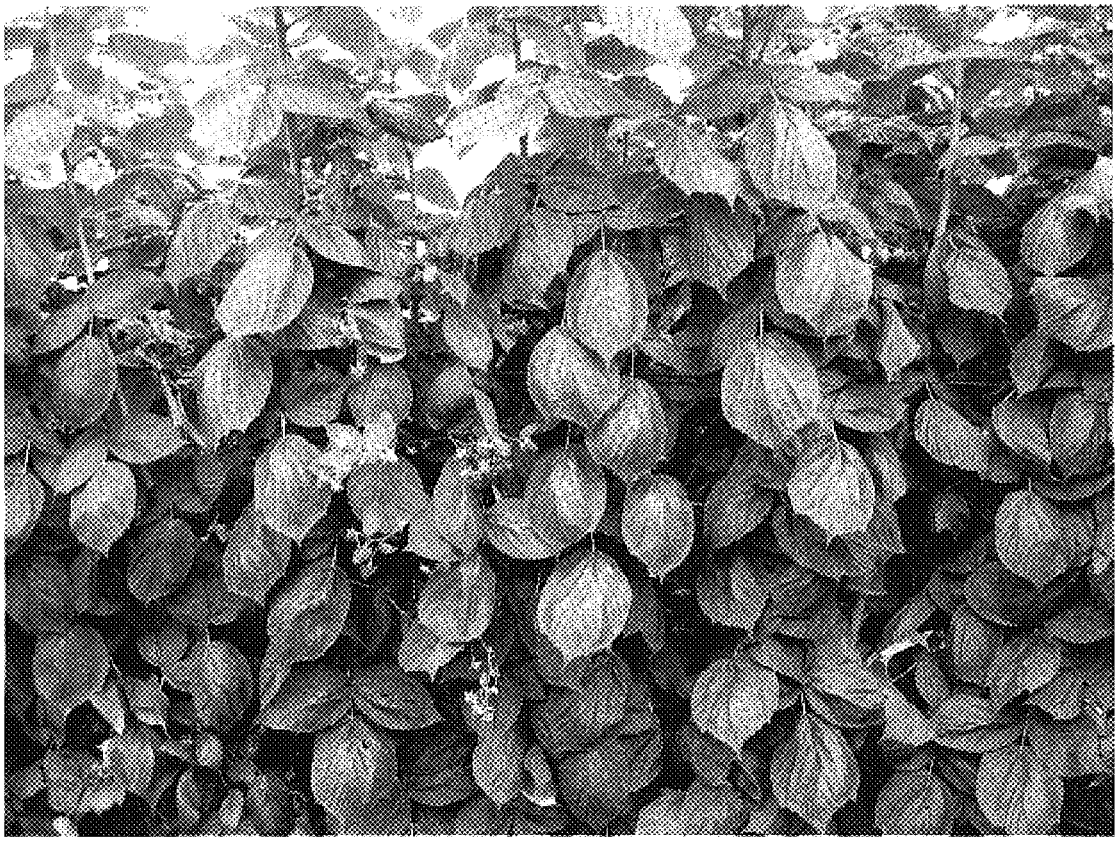
FIG. 1 shows typical primocane plant characteristics taken in the month of August.
Figure 2:
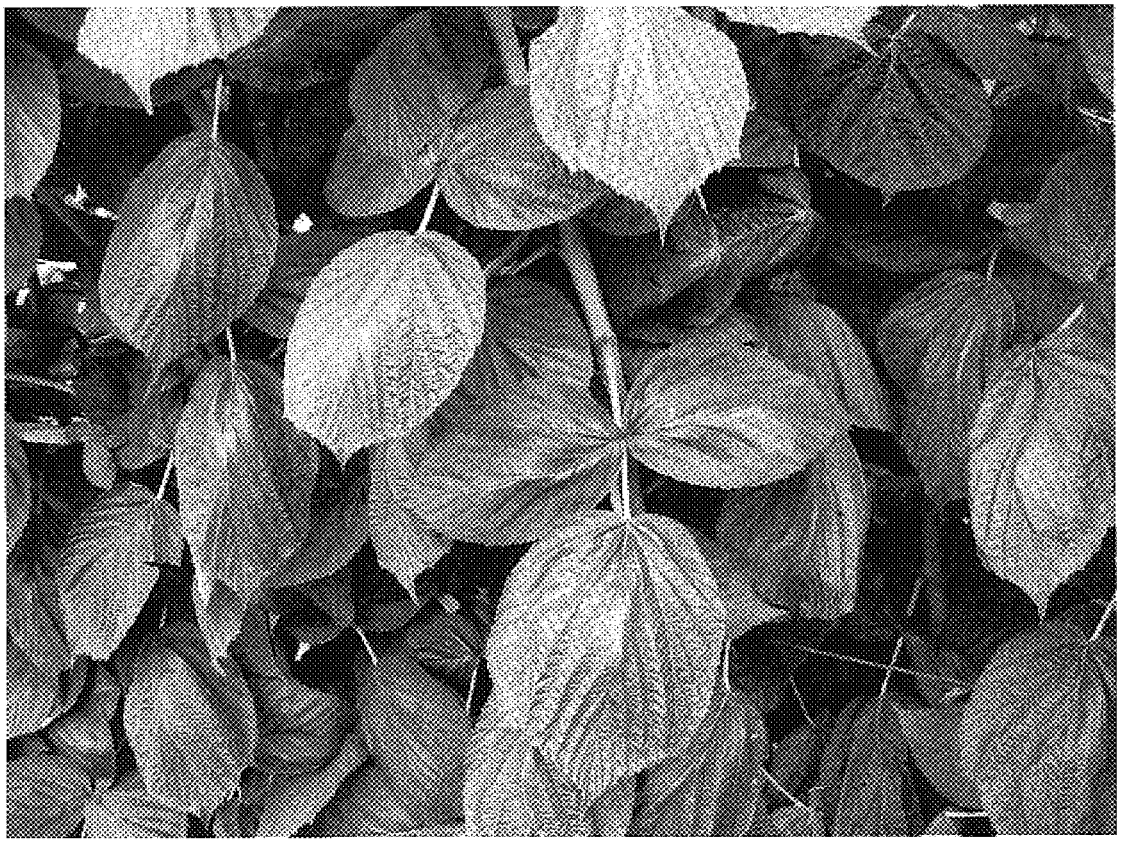
FIG. 2 shows a close-up of typical primocane foliage characteristics taken in the month of August.
Figure 3:
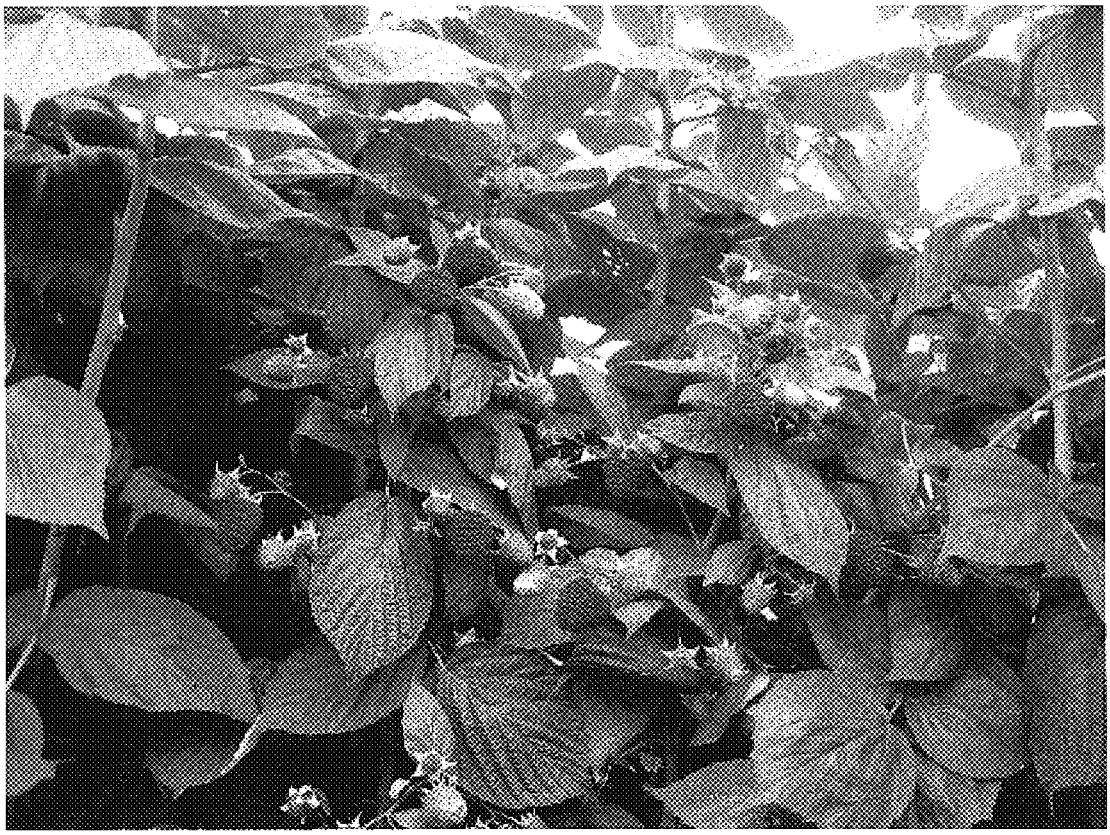
FIG. 3 shows typical primocane field fruiting characteristics taken in the month of August.
Figure 4:
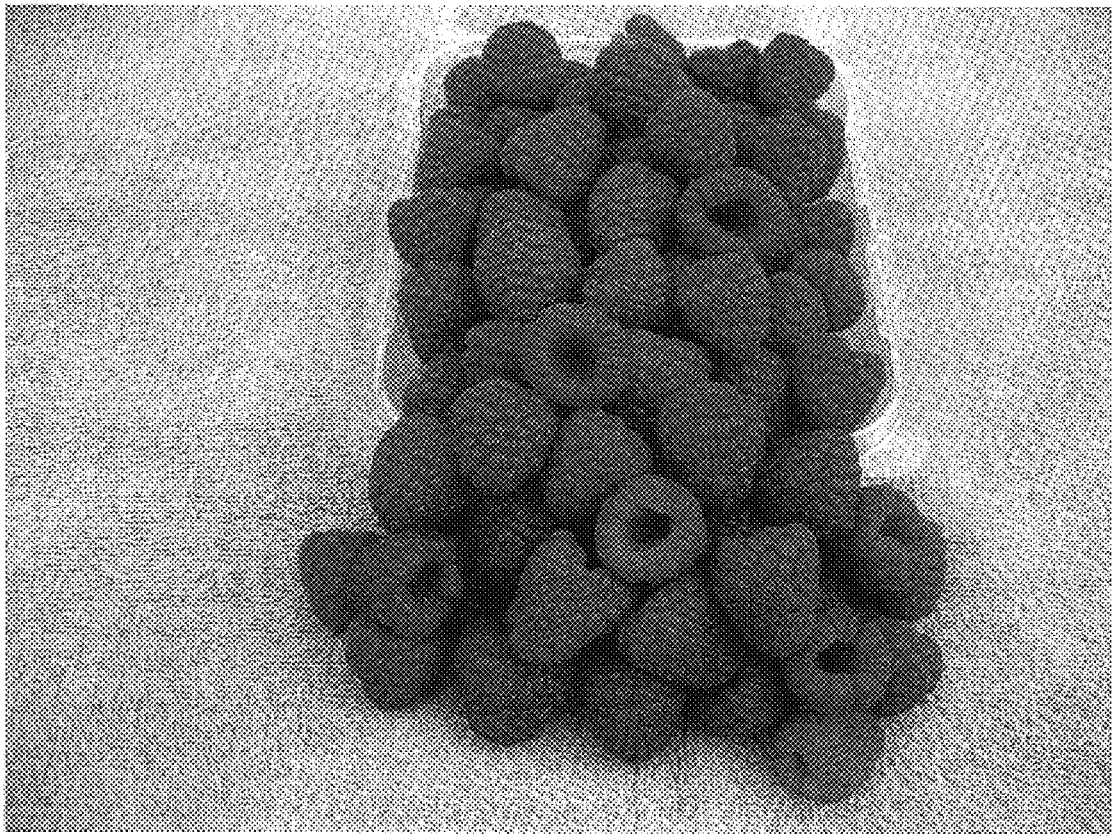
FIG. 4 shows typical primocane fruit characteristics taken in the month of October.

'PS-1852' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'PS-1852', unless otherwise noted, is based on observations taken during the 2006 growing season in Watsonville, Calif. Primocane measurements and ratings were taken from plants of 'PS-1852' dug from a nursery located in San Joaquin County, Calif., during the middle of December, 2005, and planted approximately 3 to 4 weeks later in Watsonville, Calif. The approximate age of the observed primocane plants is 7 to 8 months. Floricane measurements and ratings were taken from the plants of 'PS-1852' dug from a nursery located in San Joaquin County, Calif., during the middle of December, 2004, and planted approximately 3 to 4 weeks later in Watsonville, Calif. The approximate age of the observed floricane plants is 16 to 18 months. Yield observations and fruit quality characteristics are averaged from three years of data collected from the 2004 through 2006 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows the Munsell Book of Colors, Munsell Color, Baltimore, Md. (1976).

In comparison to the similar raspberry varieties 'PS-1049' and 'PS-1703', the fruit characteristics of 'PS-1852' differ as described in Table 2:

TABLE 2

FRUIT CHARACTERISTICS

| Characteristic | 'PS-1852' | 'PS-1049' (U.S. PP 10,142) | 'PS-1703' (U.S. PP 15,151) |
|---|---|---|---|
| Color mature fruit | 5R 3/6 to 3/8 Medium red | 5R 3/6 to 3/8 Medium red | 5R 3/10 to 3/8 Medium red |
| Color achenes | 10YR 7/4 to 8/4 | 10YR 7/4 to 8/4 | 10YR 7/4 to 8/4 |
| Fruit Length (cm) | 2.3 | 1.9 | 2.1 |
| Fruit Width (cm) | 2.0 | 1.8 | 1.8 |
| Length/Width Ratio | 1.1 Slightly longer than broad | 1.1 Slightly longer than broad | 1.2 Slightly longer than broad |
| Seed weight (mg) | 1.8 | 1.5 | 1.6 |
| Druplets per berry | 113 | 104 | 113 |
| Fruit size | Large | Medium | Medium |
| Predominant shape | Conical | Conical | Conical |
| Evenness of color | Slightly uneven | Even | Even |
| Glossiness | Medium | Medium | Strong |
| Adherence of receptacle | Weak | Weak | Weak |
| Firmness of flesh | Firm | Very firm | Firm |
| Firmness of skin | Medium | Very firm | Medium |

In comparison to the similar raspberry varieties 'PS-1049' and 'PS-1730', the plant characteristics of 'PS-1852' differ as described in Table 3:

TABLE 3

PLANT CHARACTERISTICS

| Characteristic | 'PS-1852' | 'PS-1049' (U.S. PP 10,142) | 'PS-1703' (U.S. PP 15,151) |
|---|---|---|---|
| General: | | | |
| Habit | Upright | Semi-upright | Semi-upright |
| Size | Large | Medium | Medium |
| Productivity | Medium | High | High |
| Self fruitfulness | Yes | Yes | Yes |
| Type of bearing | Everbearing | Everbearing | Everbearing |
| Primocane: | | | |
| Color | 10Y 7/4 to 7/6 Medium yellow-green | 5GY 7/4 to 6/4 Light green-yellow | 7.5GY 6/2 to 6/4 Medium to light green-yellow |
| Length (m) | 2.2 | 2.0 | 1.8 |

TABLE 3-continued

PLANT CHARACTERISTICS

| Characteristic | 'PS-1852' | 'PS-1049' (U.S. PP 10,142) | 'PS-1703' (U.S. PP 15,151) |
|---|---|---|---|
| Basal diameter (mm) | 18.6 | 16.4 | 15.3 |
| Diameter central ⅓ (mm) | 12.3 | 11.3 | 10.9 |
| Lateral length (cm) | 46.3 | 57.4 | 64.6 |
| No. fruiting laterals per cane | 10 | 14 | 13 |
| % of cane length fruiting | 27% | 40% | 46% |
| Internode length (of central ⅓ cm) | 3.8 | 5.0 | 5.8 |
| Anthocyanin coloration | Weak to medium | Weak to medium | Medium to strong |
| Pubescence | Absent | Absent | Absent |
| Length of vegetative bud | Short to Medium | Short to Medium | Short to medium |
| Strength of waxy coat | Weak | Strong | Medium to strong |
| Time of flowering | Late | Medium | Early |
| Time of fruiting | Late | Medium | Early |
| Length of fruiting season | Medium | Long | Long |
| % of total yield | 38% | 54% | 52% |
| Flowering period | Early August to Late November | Late June to Late November | Early June to Late November |
| Harvest period | Early September to Late December | Late July to Late December | Early July to Late December |
| Primocane fruit weight (g) | 3.7 | 2.8 | 3.1 |
| Primocane yield (g/plant) | 1,037 | 1,841 | 1,956 |
| Young Shoots: | | | |
| Number | Medium | Medium | Medium |
| Anthocyanin coloration | Present | Present | Present |
| Anthocyanin intensity | Very weak to weak | Very weak to weak | Absent to very weak |
| Thorns: | | | |
| Color | 7.5RP 3/6 Purple | 7.5RP 3/6 Purple | 7.5RP 3/6 Purple |
| Length central ⅓ (mm) | 2.3 | 2.2 | 1.7 |
| Presence on cane | Present | Present | Present |
| Density on cane | Medium to dense | Medium | Medium |
| Texture | Rigid | Rigid | Rigid |
| Attitude of the tip | Horizontal | Horizontal | Horizontal |
| Floricane: | | | |
| Color | 2.5YR 3/4 to 7.5YR 4/6 Brownish-purple | 5YR 4/4 to 4/6 Brown | 5YR 4/4 to 4/6 Brown |
| Length (m) | 1.6 | 1.3 | 1.1 |
| Length vegetative bud (mm) | Short | Long | Short |
| Strength of waxy coat | Weak | Strong | Medium to strong |
| Fruiting lateral attitude | Erect to semi-erect | Erect to semi-erect | Horizontal to drooping |

TABLE 3-continued

PLANT CHARACTERISTICS

| Characteristic | 'PS-1852' | 'PS-1049' (U.S. PP 10,142) | 'PS-1703' (U.S. PP 15,151) |
|---|---|---|---|
| Time bud burst | Medium to late | Medium | Medium |
| Time of flowering | Early | Medium | Medium |
| Time of fruiting | Early | Medium | Medium |
| Length of fruiting season | Medium to long | Medium to long | Medium to long |
| % of total yield | 62% | 46% | 48% |
| Flowering period | Early April to Late June | Late April to Late June | Mid April to Late June |
| Harvest period | Early May to Late July | Late May to Late July | Early May to Late July |
| Floricane fruit weight (g) | 3.2 | 2.6 | 2.8 |
| Floricane yield (g/plant) | 1,684 | 1,582 | 1,811 |

In comparison to the similar raspberry varieties 'PS-1049' and 'PS-1703', the foliage characteristics of 'PS-1852' differ as described in Table 4:

TABLE 4

FOLIAGE CHARACTERISTICS

| Characteristic | 'PS-1852' (3 Foliate) | 'PS-1049' (U.S. PP 10,142) (3 Foliate) | 'PS-1703' (U.S. PP 15,151) (5 Foliate) |
|---|---|---|---|
| General: | | | |
| Color of upper surface | 7.5GY 3/4 to 3/6 Medium green | 7.5GY 3/4 to 4/4 Medium green yellow | 7.5GY 2/4 to 3/4 Medium to Dark Green |
| Color of lower surface | 5GY 6/2 to 7/2 Light to Pale grey-green | 5GY 5/4 to 6/4 Pale yellow-green | 5GY 6/2 to 7/2 Light to Pale grey-green |
| Shape in cross section | Strongly concave | Slightly concave | Slightly concave to slightly convex |
| Arrangement | Compound | Compound | Compound |
| Relief between veins | Very strong | Medium | Medium to strong |
| Glossiness | Weak | Weak | Medium |
| Number of leaflets/leaf | Always 3 | Equal 3-5 | Mostly 5 |
| Terminal Leaflet: | | | |
| Length (cm) | 13.6 | 15.2 | 13.5 |
| Width (cm) | 10.0 | 10.9 | 7.0 |
| Length/Width Ratio | 1.4 Longer than broad | 1.4 Longer than broad | 1.9 Much longer than broad |
| Size | Medium to large | Medium to large | Medium to small |
| Shape | Cordate | Cordate | Lobed oblique |
| Shape of base | Cordate | Cordate | Acute |
| Shape of tip | Acuminate | Acuminate | Acuminate |
| Margins | Biserrate | Biserrate | Biserrate |
| Lateral Leaflet: | | | |
| Length (cm) | 11.3 | 12.4 | 11.6 |
| Width (cm) | 7.4 | 7.6 | 7.0 |
| Rachis length (cm) | 3.8 | 3.9 | 1.4 |
| Orientation | Opposite | Opposite | Opposite |
| Arrangement | Compound | Compound | Compound |
| Shape | Ovate | Ovate | Oblique |

TABLE 4-continued

| FOLIAGE CHARACTERISTICS | | | |
|---|---|---|---|
| Characteristic | 'PS-1852' (3 Foliate) | 'PS-1049' (U.S. PP 10,142) (3 Foliate) | 'PS-1703' (U.S. PP 15,151) (5 Foliate) |
| Overlapping | Touching | Touching | Free |
| Shape of the base | Acute rounded | Oblique rounded | Acute oblique |
| Shape of the tip | Acuminate | Acuminate | Acuminate |
| Margins | Biserrate | Biserrate | Biserrate |
| Petiole: | | | |
| Length (cm) | 5.1 | 6.0 | 6.2 |
| Width (mm) | 3.4 | 3.0 | 3.5 |
| Thorn presence | Yes | Yes | Yes |
| Thorn orientation | Erect | Erect | Erect |
| Anthocyanin coloration of upper surface | Absent to very weak | Absent to very weak | Medium to strong |
| Pigmentation of lower surface | Light green-yellow | Light green-yellow | Light green-yellow |
| Stipule length (cm) | 1.1 | 1.1 | 1.1 |
| Stipule orientation | Erect | Erect | Erect |

In comparison to the similar raspberry varieties 'PS-1049' and 'PS-1703', the flower characteristics of 'PS-1852' differ as described in Table 5:

TABLE 5

| FLOWER CHARACTERISTICS | | | |
|---|---|---|---|
| Characteristic | 'PS-1852' | 'PS-1049' (U.S. PP 10,142) | 'PS-1703' (U.S. PP 15,151) |
| Petal Color | N 9.5/90% R to N 9.25/84.2% R White | N 9.5/90% R to N 9.25/84.2% R White | N 9.5/90% R to N 9.25/84.2% R White |

TABLE 5-continued

| FLOWER CHARACTERISTICS | | | |
|---|---|---|---|
| Characteristic | 'PS-1852' | 'PS-1049' (U.S. PP 10,142) | 'PS-1703' (U.S. PP 15,151) |
| Flower diameter (cm) | 2.0 | 1.7 | 1.7 |
| Size | Medium | Medium | Medium |
| Petal Length (mm) | 5.8 | 5.8 | 6.4 |
| Petal width (mm) | 2.8 | 2.7 | 2.7 |
| Petal width/ width ratio | 2.1 Much longer than broad | 2.2 Much longer than broad | 2.4 Much longer than broad |
| No. petals/ flower | 5.0 | 5.0 | 5.0 |
| No. sepals/ flower | 5.0 | 5.0 | 5.2 |
| Pedicel no. spines | Few | Many | Medium |
| Peduncle anthocyanin presence | Present | Present | Present |
| Peduncle anthocyanin intensity | Medium | Very weak | Very weak |

In comparison to the similar raspberry varieties 'PS-1049' and 'PS-1703', the pest and disease reactions of 'PS-1852' differ as described in Table 6:

TABLE 6

| PEST AND DISEASE REACTIONS | | | |
|---|---|---|---|
| Characteristic | 'PS-1852' | 'PS-1049' (U.S. PP 10,142) | 'PS-1703' (U.S. PP 15,151) |
| Two spotted spider mite | Susceptible | Susceptible | Susceptible |
| Grey fruit mold | Susceptible | Susceptible | Susceptible |
| Powdery mildew | Moderately Susceptible | Moderately Susceptible | Moderately Susceptible |
| Yellow rust | Moderately Susceptible | Moderately Susceptible | Moderately Resistant |

I claim:

1. A new and distinct raspberry plant known as 'PS-1852', as herein described and illustrated by the characteristics set forth above.

* * * * *